United States Patent [19]

Gierhart

[11] Patent Number: 4,485,173

[45] Date of Patent: Nov. 27, 1984

[54] PREPARATION OF FATS AND OILS

[75] Inventor: Dennis L. Gierhart, Linden, N.J.

[73] Assignee: CPC International Inc., Englewood Cliffs, N.J.

[21] Appl. No.: 420,462

[22] Filed: Sep. 20, 1982

Related U.S. Application Data

[63] Continuation of Ser. No. 227,022, Jan. 19, 1981, abandoned.

[51] Int. Cl.³ .................................................. C12P 7/64
[52] U.S. Cl. .................................... 435/134; 435/244; 435/253; 435/255; 435/261; 435/921; 435/940; 435/944
[58] Field of Search .................. 426/20, 33, 60, 7; 435/134, 163, 184, 244, 249, 253, 255, 261, 921, 940, 944

[56] References Cited

U.S. PATENT DOCUMENTS

| | | | |
|---|---|---|---|
| 3,108,878 | 10/1963 | Higashiuchi et al. | 426/21 |
| 3,293,145 | 12/1966 | Leavitt et al. | 435/872 X |
| 3,445,337 | 5/1969 | Spencer et al. | 435/134 X |
| 4,032,405 | 6/1977 | Tatsumi et al. | 435/134 |
| 4,275,081 | 6/1981 | Coleman et al. | 426/33 |

OTHER PUBLICATIONS

Deinema, M. H., "Intra- and Extra-Cellular Lipid Production by Yeasts", H. Veenman and Zonen N. V., Wageningen, Netherlands, 1961, pp. 1-54.
Lissant, K. J., "Emulsion and Emulsion Technology", Part 1, Marcel Dekker, Inc., N.Y. 1974, pp. 268-275.

*Primary Examiner*—Robert Yoncoskie

[57] ABSTRACT

A process for the production of fats and oils, and particularly fats and oils rich in triglycerides, comprising cultivating microorganisms capable of synthesizing the fats and oils in a medium containing an emulsion of at least one fatty acid having 10 to 20 carbon atoms, followed by separation of the fats and oils from the cultivated microorganisms.

12 Claims, No Drawings

PREPARATION OF FATS AND OILS

This application is a continuation of application Ser. No. 227,022, filed 1/19/81 now abandoned.

The present invention relates to a process for the production of fats and oils, and particularly fats and oils rich in triglycerides, from microbial sources.

It is well known that fats and oils can be produced by cultivating an oil-synthesizing microorganism, including algae, bacteria, molds and yeast. Such microorganisms synthesize oils and fats in the ordinary course of their cellulose metabolism. Extensive research has been carried out in an effort to identify microorganisms, media and conditions which would permit economically practical oil production.

One field of production of fats and oils by fermentation which has received particular attention is the field of producing cacao butter substitutes. Cacao butter is a naturally-occurring substance which contains large quantities of 1,3-disaturated-2-unsaturated triglycerides. These triglycerides include 1-stearoyl-2-oleoyl-3-palmitoyl triglycerides and 1,3-dipalmitoyl-2-oleoyl triglycerides. A process for producing triglycerides rich in the foregoing compounds is described in U.S. Pat. No. 4,032,405, granted on June 28, 1977.

As described in this patent, a cacao-butter substitute is produced by cultivating a microorganism from the genus Endomyces, Rhodotorula, Lipomyces or Rhodospordium under aerobic conditions, followed by collecting the cells and isolating the fats and oils rich in 1,3-disaturated-2-unsaturated triglycerides from the cells. The medium employed in the fermentation process of the foregoing patent generally includes a source of assimilable nitrogen, and a carbon source preferably in the form of an aldose or a di- or polysaccharide. The resulting cells are collected and from them is isolated a mixture of the fats and oils which are rich in 1,3-disaturated-2-unsaturated triglycerides.

Improvements in the process as described in the foregoing patent are described in copending application Ser. No. 904,099, filed May 8, 1978, now abandoned. As described in that copending application, it has been found that the yield of the fats and oils can be increased and the distribution of the particular fats and oils can be controlled when the fermentation medium includes a carbon nutrient source in the form of one or more fatty acids containing between 10 and 20 carbon atoms. For example, it has been found that the ratio of saturated to unsaturated acid groups of glyceryl oils may be controlled by employing in the fermentation medium the very acids which form the fatty acid portion of cacao butter, namely palmitic, oleic and stearic acids. Further improvements on the use of combined fatty acids in the fermentation medium for controlling the amounts of fatty acids in glyceryl oils are set forth in copending application Ser. No. 416,745 filed concurrently herewith.

While the process described in the foregoing copending application represents a distinct improvement in both the yield and acid distribution in fat and oil fermentation processes, there is nevertheless room for further improvement. It is thus desirable to investigate the factors affecting the production of triglyceride oils produced but also the control of the distribution of the acid component of the triglycerides themselves.

It is accordingly an object of this invention to provide a process for the production of fats and oils by fermentation in which the yields of such fats and oils are dramatically increased.

It is a more specific object of the present invention to provide a process for the production of fats and oils, and particularly fats and oils rich in triglycerides from microbial sources, wherein the yield of the desirable saturated fats and oils is increased with shortened reaction time while the yield of the less desirable unsaturated fats and oils is decreased.

The concepts of the present invention reside in a process for the production of fats and oils, and particularly fats and oils which are rich in triglycerides, wherein yeast cells which are capable of synthesizing the fats and oils are cultivated in a medium containing an emulsion of at least one fatty acid contining 10 to 20 carbon atoms. It has been found that the use of an emulsion of the fatty acid component of the fermentation medium increases the availability of the fatty acids during their assimilation by the yeast cells to thereby further increase the yields of the fats and oils produced while controlling the acid distribution of the acid components forming the triglycerides.

The process of the present invention is particularly well suited for use in the production of fats and oils of the type which are predominant in cacao butter. It has been found, in accordance with one embodiment, that the production of such oils can be significantly increased where the fermentation medium is formulated to include an emulsion of palmitic, oleic and stearic acids.

In accordance with one embodiment of the invention, it has been found that the use of a desaturase enzyme inhibitor promotes a higher ratio of stearic to oleic acid radicals present in the resulting triglyceride oils. Without limiting the invention as to theory, it is believed that the desaturase enzyme inhibitor serves to minimize the effect of intracellular desaturase which in turn prevents desaturation of the stearic acid. Thus, the use of the desaturase enzyme inhibitor results in increased stearic acid levels found in the resulting triglycerides.

While the present invention will be described hereinafter with reference to the production of fats and oils of the type which are predominant in cacao butter, that is triglycerides containing 1,3-distearoyl-2-oleoyl triglycerides, 1-stearoyl-2-oleoyl-3-palmitoyl triglycerides and 1,3-dipalmitoyl-2-oleoyl triglycerides, it will be understood by those skilled in the art that the concepts of the present invention may likewise be used in the production of other fats and oils by fermentation.

The microorganisms useful in the practice of this invention may be characterized as oil synthesizing yeasts; such yeasts are well known and available to the art. For example, a number of them are described in U.S. Pat. No. 4,032,405, the disclosure of which is incorporated herein by reference. Particularly preferred for use in the practice of this invention are species from the genus Rhodosporidium, Lipomyces, Candida, Endomyces, Saccharomyces, Rhodotorula, Trichosporon or Torulopsis.

Such oil-synthesizing yeasts are well known and can be isolated by conventional techniques from native sources such as leaves, vegetable stems and the like. It is generally more convenient, however, to obtain such yeasts from various culture storage deposits including, for example the American Type Culture Collection. For economic reasons, it is generally preferred to employ an oil-synthesizing yeast which has a tendency to synthesize and store large amounts of oils. Yeasts having the ability to accumulate 20% oil, and preferably at least 30% oil, on a standard culture medium (such as glucose, ammonium salts and minerals) are generally preferred.

The growth and/or fermentation medium providing nutrients for the cultivation of the particular yeast species to employ depends somewhat on the particular yeast selected for use in the process of this invention. In general, such media are dilute aqueous basic solutions containing carbon and nitrogen nutrient sources, generally in amounts less than 6% by weight based on the weight of the medium. Preferred media are generally adjusted or buffered so that the pH ranges between about 4.0 and 9.0, and preferably 5 to 8.5, as is conventional for optimum yeast cultivation.

As the nitrogen nutrient source, use can be made of any of a variety of conventional nitrogen-containing compounds frequently used as nutrients for microbial growth. Preferred nitrogen compounds include asparagine, glutamine, peptones and the like. In addition, other nitrogen-containing compounds such as ammonium salts and urea may likewise be used.

In general, the nitrogen nutrient source serves to promote growth of the yeast, while the carbon nutrient referred to above serves to promote fat accumulation in the yeast cells. Thus, high nitrogen-to-carbon ratios are useful in promoting growth of the cells while high carbon-to-nitrogen ratios maximize fat accumulation.

One nitrogen-containing nutrient which is particularly well suited for use in the practice of this invention is cornsteep, the aqueous liquor formed in the conventional corn-wet-milling process in which dry corn is soaked in warm dilute sulfuric acid. Cornsteep is composed of about 25% by weight of crude protein (8% nitrogen by weight) as well as small amounts of ash, sugars and other beneficial culture constituents. While cornsteep can be used alone as an inexpensive but yet complete nitrogen nutrient source, it can be formulated with other conventional nitrogen nutrient sources well known to those skilled in the art.

The medium should also include any one or more of the known essential metabolic mineral salts, including the salts of potassium, sodium, calcium, magnesium, iron or the like. In addition, secondary nutrients such as vitamins and amino acids are likewise desirable, particularly where the cultivation period for the yeast is extensive.

The fermentation medium employed in the practice of this invention also contains, in accordance with an important concept of the invention, a carbon source. As has been described briefly above, the fermentation medium should contain a predominant amount of one or more fatty acids containing between 10 and 20 carbon atoms. Because it is believed, again without limiting the invention as to theory, that the yeast cells utilize the fatty acids in their metabolism, it is preferred that the fatty acid content of the fermentation medium constitute at least 10%, and preferably 40% or higher, of the total carbon source. In that way, the fatty acids, to the extent they serve to modify the metabolism of the yeast cells to produce triglyceride oils having a particular fatty acid content, are not masked by the presence of other carbon nutrient sources in the fermentation medium.

The fatty acid or acids employed as the carbon source in the practice of this invention may be obtained from any of a variety of known sources. For example, palmitic acid ($C_{16}:0$), stearic acid ($C_{18}:0$) or oleic acid ($C_{18}:1$) can be obtained commercially, either in the form of the free acid or salts such as the sodium salt. These more common fatty acids can be employed alone or in mixture with others. Polyunsaturated fatty acids, such as linoleic acid ($C_{18}:2$), linolenic acid ($C_{18}:3$), and other fatty acids containing 16 to 20 carbon atoms may also be obtained in pure form but are more readily available in the less expensive form of commercial mixtures, such as soap stock.

The composition of the fatty acid employed is important to the extent that each fatty acid causes a unique type of shift in the oil-synthesizing metabolism of a given yeast species. When use is made of a mixture of fatty acids, their combined effect is an interaction to result in the metabolic mixtures of triglycerides containing the various fatty acids present in the fermentation medium.

However, accurate prediction of the precise yield in oil composition to be obtained from any particular fatty acid carbon source is largely empirically based. Conventional analytical procedures permit the determination of the yield in composition of oils produced from any particular carbon sources, and hence routine experimentation permits the ready identification of fatty acid carbon sources suitable for the production of any particular oil.

Some generalizations in the form of general rules have been determined, however. For example, the presence of a fatty acid of any given carbon length in the carbon source ordinarily results in the increase in the proportion of triglyceride esters containing that fatty acid as a component of the triglyceride. Similarly, the degree of saturation and/or unsaturation (and particularly polyunsaturation) in the oil produced is directly related to the corresponding saturation level of the fatty acid composition employed as the carbon source. Thus, the use of palmitic, oleic and stearic acids as the carbon source promote the formation of oils which closely approximate those existing in cacao butter.

The conditions under which the yeast is cultivated to produce fats and oils in accordance with the process of this invention are not different from those generally employed in prior art fermentation systems. In general, the yeast employed in the practice of this invention to produce such fats and oils are generally the same as prior art processes employing the same type yeast species.

The fermentation medium has nitrogen-containing nutrient such that the amount of nitrogen present in the medium ranges from 0.005 to 1% nitrogen by weight, while the carbon nutrient present in the fermentation medium generally ranges from 0.1 to 5% carbon by weight. The temperature at which the fermentation is carried out is generally within the range of about 20 to 40 C., with higher temperatures within that range favoring the production of saturated oils while lower temperatures within the range favoring the production of unsaturated oils.

Similarly, oxygen may have some effect on the growth of the yeast cells. In general, it has been found that aerobic cultivation of the yeast cells increases the final yield of the oil produced by the microorganisms.

Once the fermentation has been allowed to carry out for the desired period of time, generally for one to seven days and preferably two to five days, the yeast cells are separated from the fermentation media by conventional means and their oil content removed. For example, the cells can first be subjected to rupture by, for example, freezing or hydrolysis, and then the oil extracted from the debris with a suitable solvent, preferably a volatile solvent to facilitate subsequent removal of the solvent from the oil.

As noted above, it is an important concept of the invention that the fatty acids present in the fermentation medium be in emulsified form. That is preferably accomplished by addition to the fermentation medium of an emulsifier which is compatible with the fatty acids employed and which does not adversely affect the metabolism of the yeast cells. In general, emulsifiers employed in the practice of this invention are ionic and non-ionic emulsifiers having an HLB above 15.

Preferred for this purpose are emulsifiers in the form of fatty acid derivatives of sorbitol and sorbitol anhydrides. Particularly preferred are non-ionic emulsifiers such as those marketed by Atlas Chemical Industries Inc. under the trademark "Tween", which are polyoxyethylene derivatives of fatty acid partial esters of sorbitol anhydrides, and those marketed under the trademark "Span", which are fatty acid partial esters of sorbitol anhydrides. Both types of emulsifiers are approved by the FDA for food use; it has surprisingly been found that they do not adversely affect the metabolism of the yeast cells in the formation of fats and oils.

In general, only enough of the emulsifier as is sufficient to emulsify the fatty acids present in the fermentation medium need be used. In general, that amount ranges from 0.0001% to 1% based on the weight of the fermentation medium. The emulsion is preferably produced by adding the emulsifier to the fatty acid or fatty acids and then providing sufficient agitation to produce a substantially homogeneous fermentation medium, either with or without the other components of the fermentation medium having been added at the time of the agitation.

In the preferred practice of the invention, the emulsion is formed by heating the fatty acid with a buffer to a pH ranging from 7 to 9, followed by autoclaving the fatty acid to sterilize it if necessary. Then the emulsifier is added and the resulting mixture homogenized. The emulsion is next subjected to rapid cooling at a rate sufficient to crystalize stearic acid particles of very small sizes. It has been found in accordance with the practice of the invention that particles sizes less than 10 microns are particularly suitable to insure that the fatty acid or acids are utilized effectively in the fermentation process.

As the carbohydrate, use is preferably made of a carbohydrate selected from the group consisting of aldoses (e.g., glucose, hexose, pentose, etc.), disaccharides such as maltose, sucrose, etc. and oligosaccharides, and preferably oligosaccharides derived from the hydrolysis of starch. Glycerol may likewise be advantageously used.

In accordance with another embodiment of this invention, it has been found that it is frequently desirable to include in the fermentation medium a desaturase enzyme inhibitor. As is described above, and without limiting the present invention as to theory, it is believed that the desaturase enzyme inhibitor serves to minimize the effect of desaturase enzyme during the fermentation, and thus tends to increase the ratio of saturated oils to unsaturated oils.

One such desaturase enzyme inhibitor which has been employed is sterculic acid, the cyclopropanoic derivative of stearic acid found in cotton seed oil. It will be understood by those skilled in the art that other inhibitors may likewise be used. Generally, the amount of such an inhibitor is an amount sufficient to inhibit the desaturase enzyme, and is normally within the range of 0.001 to 0.5% by weight, and preferably 0.01 to 0.2% by weight.

Having described the basic concepts of the present invention, reference is now made to the following examples, which are provided by way of illustration and not by way of limitation, of the practice of the present invention. In those examples, all of the percentages are percentages by weight unless otherwise indicated.

EXAMPLE 1

This example illustrates the practice of the present invention in utilizing stearic acid.

An emulsion was prepared by first heating one gram of stearic acid to about 80 C. and then mixing with it a solution of potassium phosphate having a pH of 6 to 7. The resulting mixture is then heated to 120 C. for 15 minutes to sterilize the fatty acid. Thereafter, 0.01% of a gram of the emulsifier Tween 20 was added, and the resulting mixture was subjected to a quick cooling to precipitate stearic acid crystals having sizes ranging from 1 to 10 microns. The resulting milky suspension had a pH of 6 to 7, was stable and exhibited no coalescence. That emulsion was then blended with a fermentation medium so that the resulting fermentation medium had the following overall composition:

| | |
|---|---|
| Peptone | 0.5% |
| Yeast extract | 0.1% |
| Glucose | 2.0% |
| $K_2HPO_4$ | 0.1% |
| Antibiotic | 10 g/ml |
| Emulsifier (Tween 20) | 0.01% |
| Stearic acid | 1.0% |
| $H_2O$ | 100 ml |

The composition had a pH of 5.5 to 6.0.

The fermentation medium (Sample I) was then inoculated at 28 C. with yeast cells of R. toruloides grown on a nutrient medium containing 5% glucose, 5% peptone and 1% yeast extract.

At the same time, a second medium (Sample II) was was formulated in the same manner, except that the amount of glucose was increased to 4%. Another medium, Sample III, was prepared in the same manner, except that it contained no glucose and the stearic acid level was 4% by weight.

Samples II and III were inoculated with the same inoculum at 28 C. The fermentation of Samples I, II and III was allowed to continue in a shake flask at 200 rpm for 6 days at 28 C.

Another sample (Sample IV) was formulated, inoculated and fermented in the same way as Sample I, except that the pH was adjusted to 7.5 after 2½ days. The cells from each were then harvested, and the oil recovered and analyzed.

The following results were obtained.

RESULTS

EXAMPLE 1

| | Sample | | | | | | | |
|---|---|---|---|---|---|---|---|---|
| | I | | II | | III | | IV | |
| | | x | | x | x | | | x |
| Mg. of | 200 | 225 | 217 | 388 | 407 | 350 | 469 | 542% |

-continued

| | Sample | | | | | | | |
|---|---|---|---|---|---|---|---|---|
| | I | | II | III | | IV | | |
| | | x | x | x | | | x | |
| Neutral Oil | | | | | | | | |
| % Conversion based on lipid | 20% | 23% | 22% | 39% | 21% | 17% | 47 | 54.28% |
| C:12 | .2 | .3 | .3 | | .1 | .1 | .1 | .1 |
| C:14 | .7 | 1.0 | 1.2 | | .4 | .3 | .6 | .5 |
| C:16:0 | 17.4 | 22.8 | 20.6 | | 13.2 | 10 | 15.4 | 13 |
| C:16:1 | 4.2 | 1.0 | 4.4 | | .5 | .3 | .5 | 2.1 |
| C:18:0 | 32 | 29.8 | 24.3 | | 49.2 | 48 | 39.6 | 35.2 |
| C:18:1 | 31.3 | 32.2 | 32.0 | | 25.7 | 25 | 31.4 | 35.2 |
| C:18:2 | 5.7 | 1.3 | 6.3 | | 4.0 | 9.9 | 4.7 | 7.4 |
| C:20 | .6 | .6 | .7 | | .8 | .7 | .7 | .6 |
| C:18:3 | .9 | .3 | .7 | | .3 | 1.9 | .6 | 1.4 |
| C:22 | .9 | 1.0 | 1.4 | | .6 | .6 | .8 | .7 |
| Unknowns | 4.0 | 7.1 | 4.6 | | 4.9 | 3.6 | 4.5 | 3.0 |
| Total saturates | 54 | 58 | 52 | | 65 | 59.7 | 58.3 | 51 |
| Total monounsaturates | 35.5 | 33.2 | 36.4 | | 26 | 24.8 | 31.9 | 37.8 |
| Total polyunsaturates | 6.6 | 1.6 | 7.0 | | 4.3 | 11.8 | 5.4 | 8.8 |
| Theoretical Iodine | 42.3 | 32 | 44 | | 30 | 43 | 37 | 48.6 |

The foregoing results show that the presence of carbohydrates in the fermentation medium serves to increase the levels of palmitic and oleic acid levels at the expense of stearic acid levels. In addition, the adjustment of the pH of the fermentation medium to a pH above 7 results in increased conversion.

EXAMPLE 2

This example illustrates the importance of forming the emulsifier in the fermentation medium used in accordance with the practice of the present invention.

In this example, several fermentation media were prepared, except that the procedure described in Example 1 was varied except as follows: the fermentation medium employed in this example consisted of 0.02% potassium phosphate, 0.02% Tween 20 or Tween 80 which was employed with stearic acid in accordance with the following:

| Sample | |
|---|---|
| A | Stearic acid (no homogenization, no quick cool, no emulsifier) |
| B | 0.02% Tween 20 (no homogenization or quick cool) |
| C | Stearic acid homogenized (no homogenization or quick cool) |
| D | Stearic acid homogenized with Tween 80 (no quick cool) |
| E | Stearic acid homogenized with Tween 20 (no quick cool) |
| F | Stearic acid homogenized with Tween 20 and quick cooling |
| G | Stearic acid homogenized at a pH of 4.5 but with no quick cooling. |

All of the foregoing samples were inoculated with *R. toruloides* grown in a 5-liter fermenter at 28 C. for 48 hours. The fattening phase was carried out on a shake incubator at 32 C. and 260 rpm. One gram of *R. toruloides* was added to 100 ml of lipid media. After emulsions were prepared, visual observations were noted and reported as follows:

| Sample | Observation |
|---|---|
| A | Large chunks of stearic |
| B | Same as A |
| C | Small particles of stearic |
| D | Same as C |
| E | Same as C |
| F | No particles observed |
| G | Same as C |

Just prior to harvesting from the lipid media, microscopic observations were made with the following results:

| Sample | Observation |
|---|---|
| A & B | Little or no lipid accumulation |
| C–E | 10–20% lipid accumulation |
| F | 20–40% lipid accumulation |
| G | 10–20% lipid accumulation |

The visual observations to the foregoing samples prior to inoculation show that samples A-E and G contain visual observation of particles, thus demonstrating that they were greater in size than 1 to 2 microns. The microscopic examination just prior to harvesting revealed that the greater the particle size, the less was the lipid accumulation. Samples A and B were not homogenized, and thus had the largest particles. As the particle size decreased (i.e., Samples C through E, inclusive), larger cellular lipid globules were observed.

The analytical results are shown in the following table:

| Sample | Neutral Oil (mg.) |
|---|---|
| A (No homogenization) | 50.2 mg |
| B (No homogenization - .02% Tween 20) | 54.7 |
| C (Homogenization - no emulsifier) | 103.0 |
| D (Homogenization - Tween 80) | 100.1 |
| E (Homogenization - Tween 20-no quick cool) | 106.9 |
| F (Homogenization - Tween 20-quick cool) | 139.7 |
| G (Homogenization - Tween 20-pH 4.5) | 93.7 |

The results shown in the following example illustrate that a good emulsion is essential to effective utilization of stearic acid. The factors contributing to the formation of a good emulsion are proper homogenization, a proper level of emulsifying agent, a neutral pH and a quick cooling in an ice pack. The use of an emulsifying agent without heating or melting of the fatty acid with homogenization and quick cooling is not particularly effective, the data show, with fatty acid carbon sources having high melting points. This is why the emulsion process of the present invention was developed.

Of importance to the structure and melting properties of cacao butter is the degree of unsaturation in the B-position. Listed in Table 2 is the B positional data for a given sample. This is the sterospecific method using pancreatic lipase. Luddy F. E. et al. JAOCS, Vol. 41, p. 693 1964.

TABLE 2

| Fatty Acid Composition of Triglyceride | | B-position |
|---|---|---|
| C:14 | 0.4 | .33 |
| C:16 | 26.1 | 4.7 |
| C:16:1 | 2.2 | 1.2 |
| C:17 | 1.4 | — |
| C:unknown | 0.4 | .78 |
| C:18 | 28.7 | 2.9 |

TABLE 2-continued

| Fatty Acid Composition of Triglyceride | | B-position |
|---|---|---|
| C:18:1 | 31.5 | 72 |
| C:18:2 | 7.2 | 16 |
| C:18:3 | 1.0 | 1.5 |
| C:22 | — | .3 |

The information demonstrates that the fatty acid composition can nearly be matched and triglyceride is biosynthesized with nearly the same proportions of SUS as in cacao butter.

It will be understood that various changes and modifications can be made in the details of procedure and formulation without departing from the spirit of the invention, especially as defined in the following claims.

I claim:

1. A process for the microbiological production of fats or oils comprising:
   (a) preparing a suitable growth medium comprising a carbon nutrient source having a fatty acid component containing a least one fatty acid having between 10 and 20 carbon atoms,
   (b) inoculating said growth medium with cells of a microorganism capable of synthesizing fats or oils from the growth medium,
   (c) cultivating said microorganism by maintaining the growth medium at a suitable pH and temperature to promote growth,
   (d) separating the cultivated cells from said growth medium, and
   (e) recovering the fat or oil from the cultivated cells, wherein said fatty acid component is present in the growth medium in the form of an homogenized emulsion employing an emulsifier having an HLB above 15, which emulsifier is compatible with the fatty acid component employed and which does not adversely affect the metabolism of the cultivated cells.

2. A process as defined in claim 1 wherein the fatty acid component is prepared by forming a mixture of at least one fatty acid which is normally solid at the intended fermentation temperature and an emulsifying agent, heating the mixture slightly to facilitate mixing, and homogenizing the mixture with at least a sufficient quantity of water to form an emulsion.

3. A process as defined in claim 2 wherein the homogenized emulsion is subjected to rapid cooling at a rate which is sufficient to solidify into particles of very small sizes said fatty acid which is normally solid at the intended fermentation temperature.

4. A process as defined in claim 1 which further comprises the step of increasing the pH of the fermentation medium to a level ranging from 7-9 during fermentation.

5. A process as defined in claim 1 wherein the emulsion also contains a carbohydrate.

6. A process as defined in claim 5 wherein the fatty acid constitutes at least 50% by weight of the carbon-nutrient source in the fermentation medium.

7. A process for the microbiological production of fats and oils comprising:
   (a) preparing a suitable growth medium in an emulsion form comprising a carbon nutrient source having a fatty acid component, selected from the group consisting of palmitic, oleic and stearic acids and mixtures thereof, wherein the relative concentrations of said acids are selected to produce triglycerides characteristically found in cocoa butter,
   (b) inoculating said growth medium with cells of a microorganism capable of synthesizing fats or oils from the growth medium,
   (c) cultivating said microorganism by maintaining the growth medium at a suitable pH and temperature to promote growth,
   (d) separating the cultivated cells from said growth medium, and
   (e) recovering the fat or oil in the form of 1,3-disaturated-2-unsaturated triglycerides characteristically found in cocoa butter from the cultivated cells, wherein said fatty acid component is present in the growth medium in the form of an homogenized emulsion employing an emulsifier having an HLB above 15, which emulsifier is compatible with the fatty acid component employed and which does not adversely affect the metabolism of the cultivated cells.

8. A process as defined in claim 1 or 7 in which the microorganism cultivated is a yeast.

9. A process as defined in claim 8 in which the yeast is a specie of the genus selected from the group consisting of Rhodosporidium, Lipomyces, Candida, Endomyces, Saccharomyces, Rhodotorula, Trichosporon and Torulopsis.

10. A process as defined in claim 8 wherein the microorganism is cultivated aerobically.

11. A process as defined in claim 8 wherein the microorganism is cultivated in the presence of a desaturase enzyme inhibitor in the amount of 0.001% to 0.5% by weight.

12. A process as defined in claim 8 in which the yeast comprises R. toruloides.

* * * * *